US007457710B2

(12) United States Patent
Schuermans et al.

(10) Patent No.: US 7,457,710 B2
(45) Date of Patent: Nov. 25, 2008

(54) APPARATUS AND METHOD FOR TESTING COMBUSTION

(75) Inventors: Bruno Schuermans, Basel (CH); Martin Zajadatz, Kuessaberg (DE); Christian Oliver Paschereit, Berlin (DE)

(73) Assignee: ALSTOM Technology Ltd., Baden (CH)

( * ) Notice: Subject to any disclaimer, the term of this patent is extended or adjusted under 35 U.S.C. 154(b) by 0 days.

(21) Appl. No.: 11/279,421

(22) Filed: Apr. 12, 2006
(Under 37 CFR 1.47)

(65) Prior Publication Data

US 2006/0228658 A1  Oct. 12, 2006

Related U.S. Application Data

(63) Continuation of application No. PCT/EP2004/052506, filed on Oct. 12, 2004.

(30) Foreign Application Priority Data

Oct. 14, 2003  (GB) ................... 0324074.4

(51) Int. Cl.
*F23N 5/00* (2006.01)
(52) U.S. Cl. ........................................ 702/30
(58) Field of Classification Search .............. 702/30
See application file for complete search history.

(56) References Cited

U.S. PATENT DOCUMENTS

| 3,374,661 A | 3/1968 | Foner et al. |
| 4,557,106 A | 12/1985 | Ffowcs Williams et al. |
| 5,428,951 A | 7/1995 | Wilson et al. |
| 5,797,266 A | 8/1998 | Brocard et al. |
| 6,202,401 B1 | 3/2001 | Seume et al. |

(Continued)

FOREIGN PATENT DOCUMENTS

WO  WO2005/038447  4/2005

(Continued)

OTHER PUBLICATIONS

R.A. Huls, Vibration prediction in combustion chambers by coupling finite elements and large eddy simulations, Journal of Sound and Vibration 304 (2007) 224-229, Faculty of Engineering Technology, University of Twente, CERFACS, 42 Avenue G. Coriolis, 31057 Toulouse Cedex, France, Apr. 24, 2007, p. 224-229.*

(Continued)

*Primary Examiner*—Tung S Lau
(74) *Attorney, Agent, or Firm*—Cermak Kenealy & Vaidya LLP; Adam J. Cermak

(57) ABSTRACT

A sensor 11 detects the acoustic pressure at a first location in a combustion chamber 7 of a test rig 1 and produces an input signal which is a function of the acoustic pressure. A controller 13 receives the input signal and produces an output signal which is a function of the input signal. An acoustic actuator (16-18) receives the output signal and introduces into the combustion chamber 7 at a second location an acoustic pressure which is a function of the output signal. The acoustic actuator may comprise a fuel injector 18 or a loudspeaker. By using an appropriate control algorithm, acoustic boundary conditions corresponding to a particular gas turbine combustion chamber may be produced, at least in a certain frequency range.

9 Claims, 2 Drawing Sheets

U.S. PATENT DOCUMENTS

| | | | |
|---|---|---|---|
| 6,205,765 | B1 | 3/2001 | Iasillo et al. |
| 6,461,144 | B1 | 10/2002 | Gutmark et al. |
| 6,464,489 | B1 * | 10/2002 | Gutmark et al. ............ 431/1 |
| 2002/0162317 | A1 | 11/2002 | Banaszuk et al. |

FOREIGN PATENT DOCUMENTS

| | | |
|---|---|---|
| WO | WO01/84053 | 6/2006 |

OTHER PUBLICATIONS

Paschereit, C. O., et al., "Structure and Control of Thermoacoustic in a Gas-Turbine Combustor," 1998 36th A1AA Aerospace Science Meeting Jan. 12-15, 1998, Reno NV p. 1-9.

Search Report for United Kingdom Patent App. No. GB 0324074.4 (Feb. 25, 2004).

International Search Report for PCT App. No. PCT/EP2004/052506 (Feb. 21, 2005).

International Preliminary Report on Patentability for PCT App. No. PCT/EP2004/052506 (Nov. 3, 2005).

* cited by examiner

APPARATUS AND METHOD FOR TESTING COMBUSTION

This application is a Continuation of, and claims priority under 35 U.S.C. § 120 to, International application number PCT/EP2004/052506, filed 12 Oct. 2004, and claims priority under 35 U.S.C. § 119 to Great Britain patent application number 324074.4, filed 14 Oct. 2003, the entireties of both of which are incorporated by reference herein.

BACKGROUND OF THE INVENTION

1. Field of the Invention

This invention relates to apparatus for testing the combustion of a fuel and to a method of testing the combustion of a fuel. Such testing is required, for example, when designing a burner or determining appropriate conditions for combustion of a particular fuel, especially in the field of gas turbines.

2. Brief Description of the Related Art

Thermoacoustic pulsations may limit the range of operating conditions where a modern gas turbine can operate with low emission and high efficiency performance. These pulsations are caused by complex interaction between hydrodynamic instabilities, unsteady heat release, and the acoustic field. Because of its complex nature, this phenomenon is very difficult to model or simulate accurately. Therefore, tests in a combustion test facility remain the most important tool to assess thermoacoustic behaviour of a combustion system. It is of crucial importance that the acoustic boundary conditions of the test rig are very similar to the acoustic behaviour of the gas turbine combustion chamber. The acoustic boundary conditions (or acoustic impedance) of a test facility can be changed by modifying the geometry of the test rig. However, such hardware changes are expensive and time consuming.

What is desired is apparatus which enables the acoustic boundary conditions to be modified without changing the geometry of the test rig.

SUMMARY OF THE INVENTION

The present invention provides apparatus for testing the combination of a fuel, the apparatus including a combustion chamber, a sensor which detects the acoustic pressure at a first location in the combustion chamber and produces an input signal which is a function of the acoustic pressure, a controller which receives the input signal and produces an output signal which is a function of the input signal, and an acoustic actuator which receives the output signal and which introduces into the combustion chamber at a second location an acoustic pressure which is a function of the output signal.

The invention also provides a method of testing the combustion of a fuel, in which a combustion chamber is defined downstream of a burner, the acoustic pressure is detected at a first location in the combustion chamber, an input signal is produced which is a function of the acoustic pressure, an output signal is produced which is a function of the input signal, and an acoustic pressure which is a function of the output signal is introduced into the combustion chamber at a second location so as to adjust the acoustic impedance of the combustion chamber.

The invention makes it possible to use active control techniques to modify the acoustic boundary conditions in the combustion chamber. By using an appropriate control algorithm, required acoustic boundary conditions (for example corresponding to the acoustic boundary conditions in a particular gas turbine combustion chamber) may be reproduced, at least in a certain frequency range.

Loudspeakers may be used as acoustic actuators for tests performed at atmospheric pressure. For large-scale test performed under high pressure, cyclic injection of a fuel into the hot exhaust gases in the combustion chamber may be used to acoustically excite the system. The cyclic injection results in a fluctuating release of heat; the periodic volumetric expansion associated with the heat release acts as an acoustic source.

A simple arrangement preferably comprises a water-cooled microphone placed in the combustion chamber, a band-pass filter, a time delay line, an audio amplifier, and loudspeakers. Combustion is performed and the pressure oscillations are measured by the microphone. The microphone signal is compared with the (previously) recorded pressure signal of a gas turbine. If the main resonance frequency of the gas turbine is not reproduced, the required control is applied. For this purpose, the microphone signal is connected with the input of the band-pass filter; the output of the filter is connected to the time delay line; the output of the time delay line is connected to the amplifier; and the output of the amplifier is connected to the loudspeakers. The settings of the band-pass filter are adjusted so that only signals with a frequency close to the observed instability in the gas turbine are sent to the time-delay line. The delay of the time-delay line and the gain of the amplifier are adjusted so that the response at the desired frequency is maximal. Once all the parameters of the active control have been tuned, the actual tests can be performed in the usual way, using the testing apparatus.

BRIEF DESCRIPTION OF THE DRAWINGS

The invention will be described further, by way of example only, with reference to the accompanying drawings, in which.

DETAILED DESCRIPTION OF EXEMPLARY EMBODIMENTS

Figure 1A:
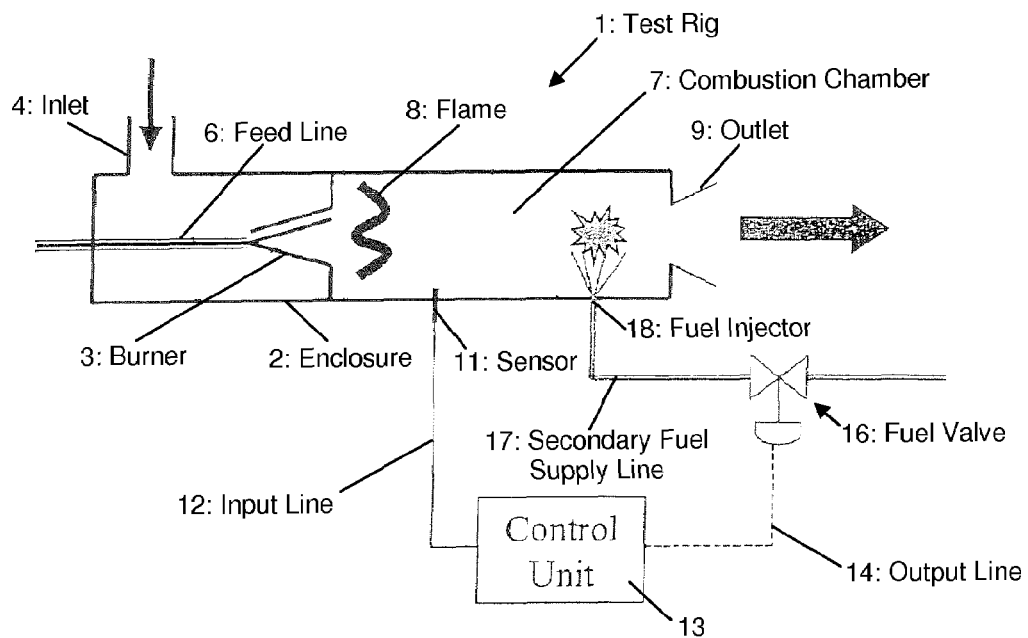
FIG. 1a is a diagrammatic representation of one embodiment of apparatus for testing combustion.

The apparatus shown in FIG. 1a includes a combustion test rig 1 including an enclosure 2 in which a burner 3 is mounted. Combustion air is supplied to the enclosure 2 through an inlet 4 upstream of the burner 3, to which fuel is supplied by a feed line 6. Downstream of the burner 3 the enclosure 2 defines a combustion chamber 7 which contains the flame 8 produced by the combustion of the fuel. Exhaust gases issue from the combustion chamber 7 through an outlet 9. The testing of combustion in the test rig may involve observation or analysis of the flame 8 and the exhaust gases using various detectors (not shown) which are well known to those skilled in the art of combustion testing and which need not be described here.

A pressure sensor 11 is arranged in the combustion chamber 7 at a location just downstream of the burner 3. The sensor 11 may be constituted by any suitable fast-response pressure transducer which can withstand the temperatures prevailing in the combustion chamber. Although a single sensor mounted in or on the wall of the enclosure 2 is shown, it may be possible to use more than one sensor and/or to mount the sensor at a distance from the wall (e.g., on the axis of the combustion chamber 7). The signal from the sensor 11 (representing the acoustic pulsations at the location of the sensor) is fed as an input signal via an input line 12 to a controller or control unit 13 arranged to generate an output signal which is a function of the input signal and which is fed via an output line 14 to a fast-response fuel valve 16. A secondary fuel supply line 17, controlled by the valve 16, is connected to a fuel injector 18 which injects fuel into the combustion chamber 7 at a location downstream of the sensor 11. Although a single injector mounted in or on the wall of the enclosure 2 has been shown, it may be preferable to use more than one injector and/or to mount the injector at a distance from the wall. The valve 16 and injector 17 together function as an acoustic actuator under the control of the control unit 13.

The control unit 13 implements a control algorithm for actively tuning the acoustic impedance of the combustion chamber 7 by means of the output signal to the acoustic actuator (16/17) as a function of the input signal to the control unit. For narrow-band impedance tuning the control unit may comprise a band-pass filter, an amplifier, and a time-delay line. For broad-band impedance tuning, an algorithm implemented on a digital signal processing board may be used.

Figure 1B:
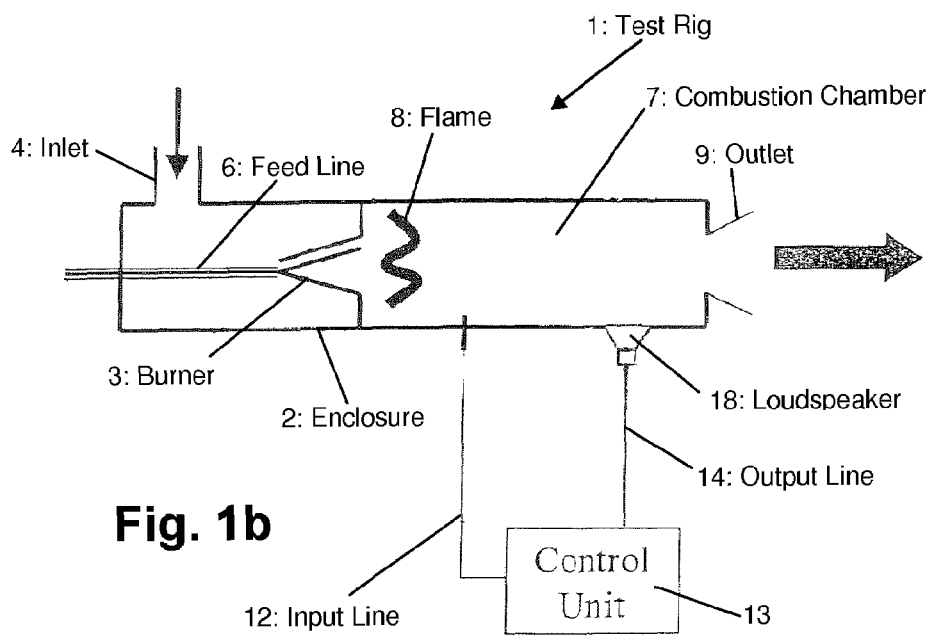
FIG. 1b is a diagrammatic representation of another embodiment of the apparatus.

The embodiment shown in FIG. 1$b$ differs from that shown in FIG. 1$a$ only in that the acoustic actuator is constituted by a loudspeaker 18, which is mounted in the wall of the enclosure 2.

The downstream acoustic boundary of the combustion system is defined by the acoustic impedance, $Z(\omega)$, at the burner exit, and is a function of angular frequency, $\omega$. Acoustic impedance is defined as the ratio between acoustic pressure (sound pressure), $p'$, and acoustic velocity (particle velocity), $u'$. (The prime ['] indicates that these are acoustic quantities, i.e. small perturbations around a mean value.)

$$Z(\omega) = p'/u' \quad [1]$$

In the following analysis:

$Z_g$ denotes the acoustic impedance of a gas turbine combustion chamber (evaluated at the exit of the burner); and $Z_t$ denotes the acoustic impedance of the test rig in the absence of active impedance tuning.

The effect of an acoustic actuator (volume source) on the acoustic field can be expressed as an additional term, $u_s'$, so that:

$$u' = p'/Z_t + u_s' \quad [2]$$

The transfer function between the volume source and the electrical signal, $e'$, received by the actuator is denoted as $H_a(\omega)$.

$$H_a(\omega) = u_s'/e' \quad [3]$$

The controller obtains the acoustic pressure, $p'$, as an input and provides the electrical signal, $e'$, as an output in accordance with a transfer function denoted as $K(\omega)$.

$$K(\omega) = e'/p' \quad [4]$$

Thus, when the controller is in operation, the following relationship between acoustic pressure and velocity at the burner exit is obtained:

$$u' = p'/Z_t + KH_a p' \quad [5]$$

The relationship [5] can be expressed as:

$$p' = Z_c u' \quad [6]$$

where $Z_c$ is the acoustic impedance of the controlled test rig.

$$Z_c = 1/(1/Z_t + KH_a) \quad [7]$$

In order to reproduce the impedance of the gas turbine combustion chamber, $$Z_c = Z_g \quad [8]$$

Accordingly, $$K = (1/Z_g - 1/Z_t)/H_a \quad [9]$$

$H_a$, $Z_t$, and $Z_g$ may be obtained by computation or experiment, and the transfer function, $K$, may be implemented on a digital signal processing board. Care should be taken to ensure that the controller implementing the transfer function is stable and proper. If this is not possible over the full frequency range, a stable proper controller should be obtained that approximates K in a frequency range of interest.

If information about $H_a$, $Z_t$, and $Z_g$ is lacking or if the impedance of the gas turbine combustion chamber only needs to be reproduced in a narrow frequency band, the controller may comprise a band-pass filter (in which the pass band corresponds to the frequency range of interest), an amplifier (gain), and a time delay line (to set the phase).

Figure 2:
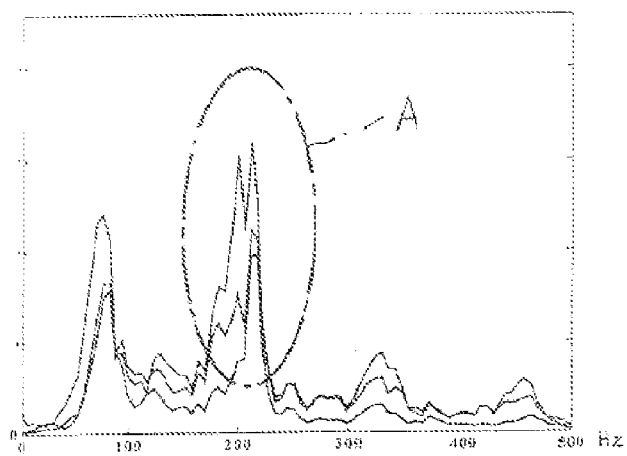
FIG. 2 is a graph of pressure (in arbitrary units) versus frequency (in Hz), showing a simulated pressure spectrum for a hypothetical gas turbine configuration.
Figure 3:
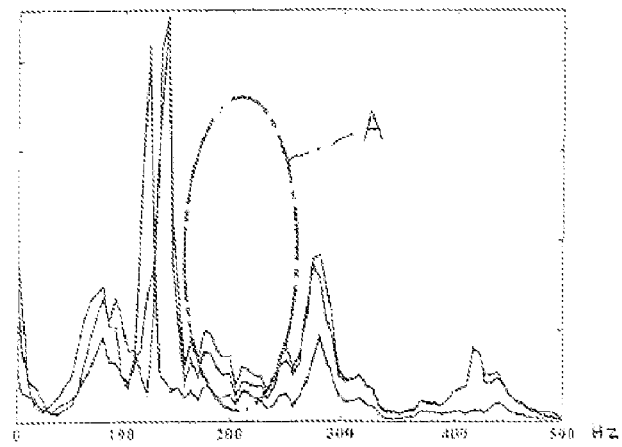
FIG. 3 is a graph similar to FIG. 2, but for a combustion testing apparatus without active impedance control.
Figure 4:
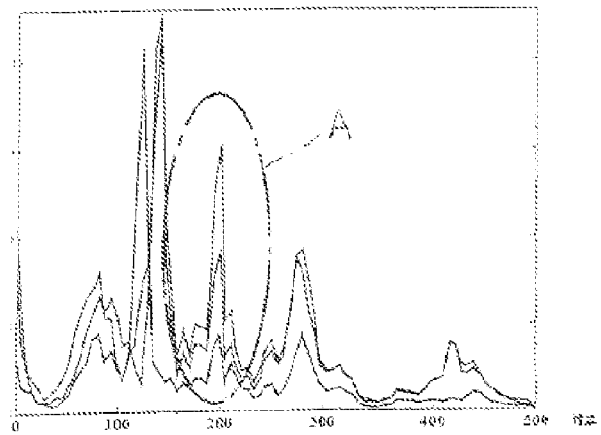
FIG. 4 is a graph similar to FIG. 3, but with active impedance control.

The results of numerical simulations (computer simulations) which have been carried out to test the principle of active impedance tuning are shown in the pressure spectra of FIGS. 2 to 4. In the (simulated) pressure spectrum of a (hypothetical) gas turbine combustion system, as shown in FIG. 2, it can be seen that strong peaks occur at about 200 Hz (region "A"). In the (simulated) pressure spectrum of a test rig without active impedance tuning, as shown in FIG. 3, there is no peak at about 200 Hz. By providing active impedance control as described above, it is possible to reproduce a peak at about 200 Hz in the (simulated) pressure spectrum of the test rig, as shown in FIG. 4.

While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A test rig for testing the combustion of a fuel, the test rig comprising:

a combustion chamber; and means for replicating the acoustic impedance of a combustor in the test rig, said replicating means comprising:

a sensor configured and arranged to detect the acoustic pressure at a first location in the combustion chamber and to produce an input signal which is a function of the acoustic pressure;

a controller in communication with the sensor to receive the input signal and configured and arranged to produce an output signal which is a function of the input signal and the acoustic impedance of the combustor; and an acoustic actuator configured and arranged to receive the output signal and introduce into the combustion chamber at a second location an acoustic pressure which is a function of the output signal.

2. A test rig as claimed in claim 1, wherein the actuator comprises a loudspeaker.

3. A test rig as claimed in claim 1, wherein the actuator comprises a fuel valve controlled by the output signal and a fuel injector which is connected to the fuel valve and which injects fuel into the combustion chamber.

4. A test rig as claimed in claim 1, wherein the controller comprises a digital processor.

5. A test rig as claimed in claim 1, wherein the controller comprises a band-pass filter.

6. A test rig as claimed in claim 5, wherein the controller includes an amplifier.

7. A test rig as claimed in claim 6, wherein the controller includes a time-delay line.

8. A test rig as claimed in claim 7, wherein the time-delay line is between the band-pass filter and the amplifier.

9. A method of testing the combustion of a fuel in a test rig, in which a combustion chamber is defined downstream of a burner, the method comprising:

adjusting the acoustic boundary conditions of the test rig, so as to at least in part replicate the acoustic impedance of a combustor in the test rig, the test rig comprising at least a sensor configured and arranged to detect the acoustic pressure at a first location in the combustion chamber and to produce an input signal which is a function of the acoustic pressure;

a controller in communication with the sensor to receive the input signal and configured and arranged to produce an output signal which is a function of the input signal and the acoustic impedance of the combustor; and an acoustic actuator configured and arranged to receive the output signal and introduce into the combustion chamber at a second location an acoustic pressure which is a function of the output signal;

installing said burner in said test rig; and testing said burner, including detecting the acoustic pressure at said first location in the combustion chamber;

producing an input signal which is a function of the acoustic pressure;

producing an output signal which is a function of the input signal; and introducing an acoustic pressure which is a function of the output signal into the combustion chamber at a second location, to adjust the acoustic impedance of the combustion chamber.

\* \* \* \* \*